(12) United States Patent
Li et al.

(10) Patent No.: US 7,745,607 B2
(45) Date of Patent: Jun. 29, 2010

(54) APTAMER SELECTION METHOD

(75) Inventors: Yingfu Li, Ontario (CA); Razvan Nutiu, Hamilton (CA)

(73) Assignee: McMaster University, Hamilton, Ontario (CA)

( * ) Notice: Subject to any disclaimer, the term of this patent is extended or adjusted under 35 U.S.C. 154(b) by 869 days.

(21) Appl. No.: 10/551,452

(22) PCT Filed: Mar. 31, 2004

(86) PCT No.: PCT/CA2004/000482

§ 371 (c)(1),
(2), (4) Date: Sep. 12, 2006

(87) PCT Pub. No.: WO2004/087947

PCT Pub. Date: Oct. 14, 2004

(65) Prior Publication Data

US 2007/0243529 A1      Oct. 18, 2007

Related U.S. Application Data

(60) Provisional application No. 60/458,409, filed on Mar. 31, 2003.

(51) Int. Cl.
*C07H 21/40* (2006.01)
*C12P 19/34* (2006.01)

(52) U.S. Cl. ................... 536/24.5; 536/23.1; 536/24.1; 536/24.3; 435/91.2

(58) Field of Classification Search ................ 536/24.5, 536/23.1, 24.1, 24.3; 435/91.2
See application file for complete search history.

(56) References Cited

U.S. PATENT DOCUMENTS

| 5,270,163 | A | 12/1993 | Gold et al. | |
|---|---|---|---|---|
| 5,475,096 | A | 12/1995 | Gold et al. | |
| 2002/0006620 | A1 * | 1/2002 | Short | 435/6 |
| 2002/0037506 | A1 * | 3/2002 | Lin et al. | 435/6 |

FOREIGN PATENT DOCUMENTS

WO          WO02/06827      *  1/2002

OTHER PUBLICATIONS

Hamaguchi et al. "Aptamer Beacons for the Direct Detention of Proteins". Analytical Biochemistry 294:126-131, 2001.
Davis et al. "Isolation of high affinity GTP aptamers from partially structured RNA libraries". PNAS 99(18):11616-11621, Sep. 2002.
Jhaveri et al. "In virto selection of signaling aptamers". Nature Biotechnology 18:1293-1297, Dec. 2000.
Sooter et al. "Toward automated nucleic acid enzyme selection". Biol. Chem 382:1327-1334, Sep. 2001.

* cited by examiner

*Primary Examiner*—Sue Liu
(74) *Attorney, Agent, or Firm*—Occhiuti Rohlicek & Tsao LLP

(57) ABSTRACT

The present invention provides a method for the selection of aptamer sequences and aptamers identified using the method. The method comprises immobilizing a library oligonucleotide by forming a duplex with an antisense oligonucleotide, reating the duplex molecule with a target and collecting oligonucleotide molecules which dissociate from the duplex structure.

16 Claims, 8 Drawing Sheets

A Library

AAGCTTNNNNNNNNNNNNNCTGCAGCGATTCTTGATCGNNNNNNNNNNNNNNNNNN

B ATP Aptamer

Class I

1ATP1 AxxCTTCGGAGGAGTTCTGCAGCGATxCTTGATCGGGGACGGGGGAGAAAGGTTT
1ATP2 AxxCTTCGGAGGAGTTCTGCAGCGATxCTTGATCGGGGACGGGGGAGAAAGGTGT
1ATP3 AxxCTTCGGAGGAGTTCTGCAGCGATxCTTGATCGGGGATGGGGGAGAAAGGTTT

Class II

2ATP1 AAxCTTTGGAGGAGATCxGCAGCGATTCTTGATCGTCATCGGGGAGAAGTGATA
2ATP2 AAxCTTTGGAGGAGATCxGCAGTGATTCTTGATCGCCATCGGGGAGAAGTGACA
2ATP3 AAxCTTTGGAGGAGATCxGCAGCGATTCTTGATCGCTATCGGGGAGAAGTGATA
2ATP4 AAxCTTTGGAGGAGATCxGCAGCGATTCTTGATCGCCATCGGGGAGAAGTGACA
2ATP5 AAGCTTCGGAGGAGAACTGCAGTGATxCTTGATCGCATTTTCGGGGAGAATGCC

Class III

3ATP1 AAGCTxGGAGGAGGAACTGCAGCGATTCGTGATCGGAAGGGTAACGGGGGAGGCT

Previously Selected ATP Aptamer

GCTTGGAGGAGTATTGCGGGGGAAAGC

C GTP Aptamer

Class I

1GTP1 AAGxxxGGGGTGGTTTCCGCAGTGATTCTTGATCGCGGAAGTTGGTGGGGAGGGT
1GTP2 AAGxxxGGGGTGGTTTCCGCAGCGATTCTTGATCGCGGAAGTTGGTGGGGAGGGT
1GTP3 AAGxxxGGGGTGGTTTCCGCAGCGATTCTTGATCGCGGAAGTTGGCGGGGAGGGT
1GTP4 GAGxxxGGGGTGGTTTCCGCAGCGATTCTTGATCGCGGAAGTTGTGGGGAGGGT
1GTP5 AAGxxxGGGGTGGTTTCTGCAGTGATTCTTGATCGCGGAAGTTGGTGGGGAGGGT

SEQUENCE LISTING

```
<160> NUMBER OF SEQ ID NOS: 27

<210> SEQ ID NO 1
<211> LENGTH: 30
<212> TYPE: DNA
<213> ORGANISM: Artificial Sequence
<220> FEATURE:
<223> OTHER INFORMATION: immobilized biotinylated DNA

<400> SEQUENCE: 1
taccgcaaaa aaaaacaaga atcgctgcag                                    30

<210> SEQ ID NO 2
<211> LENGTH: 91
<212> TYPE: DNA
<213> ORGANISM: Artificial Sequence
<220> FEATURE:
<223> OTHER INFORMATION: library oligonucleotide
<220> FEATURE:
<221> NAME/KEY: misc_feature
<222> LOCATION: (22)..(31)
<223> OTHER INFORMATION: n = a, c, g or t
<220> FEATURE:
<221> NAME/KEY: misc_feature
<222> LOCATION: (51)..(70)
<223> OTHER INFORMATION: n = a, c, g or t

<400> SEQUENCE: 2
cctgccacgc tccgcaagct tnnnnnnnnn nctgcagcga ttcttgatcg nnnnnnnnnn    60
nnnnnnnnnn taagcttggc acccgcatcg t                                   91

<210> SEQ ID NO 3
<211> LENGTH: 15
<212> TYPE: DNA
<213> ORGANISM: Artificial Sequence
<220> FEATURE:
<223> OTHER INFORMATION: Primer 1

<400> SEQUENCE: 3
gcggagcgtg gcagg                                                    15
```

<210> SEQ ID NO 4
<211> LENGTH: 22
<212> TYPE: DNA
<213> ORGANISM: Artificial Sequence
<220> FEATURE:
<223> OTHER INFORMATION: Primer 2
<220> FEATURE:
<221> NAME/KEY: misc_feature
<222> LOCATION: 22
<223> OTHER INFORMATION: n = "Ribo-A"

<400> SEQUENCE: 4
acgatgcggg tgccaagctt an                                              22

<210> SEQ ID NO 5
<211> LENGTH: 15
<212> TYPE: DNA
<213> ORGANISM: Artificial Sequence
<220> FEATURE:
<223> OTHER INFORMATION: Primer 3

<400> SEQUENCE: 5
cctgccacgc tccgc                                                      15

<210> SEQ ID NO 6
<211> LENGTH: 52
<212> TYPE: DNA
<213> ORGANISM: Artificial Sequence
<220> FEATURE:
<223> OTHER INFORMATION: ATP Aptamer - 1ATP1

<400> SEQUENCE: 6
acttcggagg agttctgcag cgatcttgat cggggacggg ggagaaaggt tt             52

<210> SEQ ID NO 7
<211> LENGTH: 52
<212> TYPE: DNA
<213> ORGANISM: Artificial Sequence
<220> FEATURE:
<223> OTHER INFORMATION: ATP Aptamer - 1ATP2

<400> SEQUENCE: 7
acttcggagg agttctgcag cgatcttgat cggggacggg ggagaaaggt gt             52

<210> SEQ ID NO 8
<211> LENGTH: 52
<212> TYPE: DNA
<213> ORGANISM: Artificial Sequence
<220> FEATURE:
<223> OTHER INFORMATION: ATP Aptamer - 1ATP3

<400> SEQUENCE: 8
acttcggagg agttctgcag cgatcttgat cggggatggg ggagaaaggt tt             52

<210> SEQ ID NO 9
<211> LENGTH: 53
<212> TYPE: DNA
<213> ORGANISM: Artificial Sequence
<220> FEATURE:
<223> OTHER INFORMATION: ATP Aptamer - 2 ATP1

<400> SEQUENCE: 9
aactttggag gagatcgcag cgattcttga tcgtcatcgg gggagaagtg ata            53

<210> SEQ ID NO 10

```
<211> LENGTH: 53
<212> TYPE: DNA
<213> ORGANISM: Artificial Sequence
<220> FEATURE:
<223> OTHER INFORMATION: ATP Aptamer - 2ATP2

<400> SEQUENCE: 10
aactttggag gagatcgcag tgattcttga tcgccatcgg gggagaagtg aca         53

<210> SEQ ID NO 11
<211> LENGTH: 53
<212> TYPE: DNA
<213> ORGANISM: Artificial Sequence
<220> FEATURE:
<223> OTHER INFORMATION: ATP Aptamer - 2ATP3

<400> SEQUENCE: 11
aactttggag gagatcgcag cgattcttga tcgctatcgg gggagaagtg ata         53

<210> SEQ ID NO 12
<211> LENGTH: 53
<212> TYPE: DNA
<213> ORGANISM: Artificial Sequence
<220> FEATURE:
<223> OTHER INFORMATION: ATP Aptamer - 2ATP4

<400> SEQUENCE: 12
aactttggag gagatcgcag tgattcttga tcgccatcgg gggagaagtg aca         53

<210> SEQ ID NO 13
<211> LENGTH: 54
<212> TYPE: DNA
<213> ORGANISM: Artificial Sequence
<220> FEATURE:
<223> OTHER INFORMATION: ATP Aptamer - 2ATP5

<400> SEQUENCE: 13
aagcttcgga ggagaactgc agtgatcttg atcgcatttt cgggggagaa tgcc        54

<210> SEQ ID NO 14
<211> LENGTH: 54
<212> TYPE: DNA
<213> ORGANISM: Artificial Sequence
<220> FEATURE:
<223> OTHER INFORMATION: ATP Aptamer - 3ATP1

<400> SEQUENCE: 14
aagctggagg aggaactgca gcgattcgtg atcggaaggg taacgggga ggct         54

<210> SEQ ID NO 15
<211> LENGTH: 52
<212> TYPE: DNA
<213> ORGANISM: Artificial Sequence
<220> FEATURE:
<223> OTHER INFORMATION: GTP Aptamer - 1GTP1

<400> SEQUENCE: 15 aaggggggtgg tttccgcagt gattcttgat cgcggaagtt ggtggggagg gt         52

<210> SEQ ID NO 16
<211> LENGTH: 52
<212> TYPE: DNA
<213> ORGANISM: Artificial Sequence
<220> FEATURE:
<223> OTHER INFORMATION: GTP Aptamer - 1GTP2

<400> SEQUENCE: 16
``` aaggggtgg tttccgcagc gattcttgat cgcggaagtc ggtggggagg gt         52

<210> SEQ ID NO 17
<211> LENGTH: 52
<212> TYPE: DNA
<213> ORGANISM: Artificial Sequence
<220> FEATURE:
<223> OTHER INFORMATION: GTP Aptamer - 1GTP3

<400> SEQUENCE: 17 aaggggtgg tttccgcagc gattcttgat cgcggaagtt ggcggggagg gt         52

<210> SEQ ID NO 18
<211> LENGTH: 52
<212> TYPE: DNA
<213> ORGANISM: Artificial Sequence
<220> FEATURE:
<223> OTHER INFORMATION: GTP Aptamer - 1GTP4

<400> SEQUENCE: 18 gaggggtgg tttccgcagc gattcttgat cgcggaagtt ggtggggagg gt         52

<210> SEQ ID NO 19
<211> LENGTH: 52
<212> TYPE: DNA
<213> ORGANISM: Artificial Sequence
<220> FEATURE:
<223> OTHER INFORMATION: GTP Aptamer - 1GTP5

<400> SEQUENCE: 19 aaggggtgg tttctgcagt gattcttgat cgcggaagtt ggtggggagg gt         52

<210> SEQ ID NO 20
<211> LENGTH: 88
<212> TYPE: DNA
<213> ORGANISM: Artificial Sequence
<220> FEATURE:
<223> OTHER INFORMATION: ATP Aptamer - 1ATP1 with primer domain

<400> SEQUENCE: 20
cctgccacgc tccgcacttc ggaggagttc tgcagcgatc ttgatcgggg acggggaga    60 aaggttttaa gcttggcacc cgcatcgt                                      88

<210> SEQ ID NO 21
<211> LENGTH: 89
<212> TYPE: DNA
<213> ORGANISM: Artificial Sequence
<220> FEATURE:
<223> OTHER INFORMATION: ATP Aptamer - 2ATP1 with primer domain

<400> SEQUENCE: 21
cctgccacgc tccgcaactt tggaggagat cgcagcgatt cttgatcgtc atcggggag    60 aagtgatata agcttggcac ccgcatcgt                                     89

<210> SEQ ID NO 22
<211> LENGTH: 90
<212> TYPE: DNA
<213> ORGANISM: Artificial Sequence
<220> FEATURE:
<223> OTHER INFORMATION: ATP Aptamer - 2ATP5 with primer domain

<400> SEQUENCE: 22
cctgccacgc tccgcaagct tcggaggaga actgcagtga tcttgatcgc attttcgggg   60

```
gagaatgcct aagcttggca cccgcatcgt                                              90
```

<210> SEQ ID NO 23
<211> LENGTH: 90
<212> TYPE: DNA
<213> ORGANISM: Artificial Sequence
<220> FEATURE:
<223> OTHER INFORMATION: ATP Aptamer - 3ATP1 with primer domain

<400> SEQUENCE: 23

```
cctgccacgc tccgcaagct ggaggaggaa ctgcagcgat tcgtgatcgg aagggtaacg            60
ggggaggctt aagcttggca cccgcatcgt                                              90
```

<210> SEQ ID NO 24
<211> LENGTH: 88
<212> TYPE: DNA
<213> ORGANISM: Artificial Sequence
<220> FEATURE:
<223> OTHER INFORMATION: GTP Aptamer - 1GTP1 with primer domain

<400> SEQUENCE: 24

```
cctgccacgc tccgcaaggg ggtggtttcc gcagtgattc ttgatcgcgg aagttggtgg            60
ggagggttaa gcttggcacc cgcatcgt                                                88
```

<210> SEQ ID NO 25
<211> LENGTH: 88
<212> TYPE: DNA
<213> ORGANISM: Artificial Sequence
<220> FEATURE:
<223> OTHER INFORMATION: GTP Aptamer - 1GTP2 with primer domain

<400> SEQUENCE: 25

```
cctgccacgc tccgcaaggg ggtggtttcc gcagcgattc ttgatcgcgg aagtcggtgg            60
ggagggttaa gcttggcacc cgcatcgt                                                88
```

<210> SEQ ID NO 26
<211> LENGTH: 88
<212> TYPE: DNA
<213> ORGANISM: Artificial Sequence
<220> FEATURE:
<223> OTHER INFORMATION: GTP Aptamer - 1GTP5 with primer domain

<400> SEQUENCE: 26

```
cctgccacgc tccgcaaggg ggtggtttct gcagtgattc ttgatcgcgg aagttggtgg            60
ggagggttaa gcttggcacc cgcatcgt                                                88
```

<210> SEQ ID NO 27
<211> LENGTH: 52
<212> TYPE: DNA
<213> ORGANISM: Artificial Sequence
<220> FEATURE:
<223> OTHER INFORMATION: Library sequence
<220> FEATURE:
<221> NAME/KEY: misc_feature
<222> LOCATION: (7)..(16)
<223> OTHER INFORMATION: n = a, c, g or t
<220> FEATURE:
<221> NAME/KEY: misc_feature
<222> LOCATION: (33)..(52)
<223> OTHER INFORMATION: n = a, c, g or t

<400> SEQUENCE: 27

```
aagcttnnnn nnnnnnctgc agcgattgat cgnnnnnnnn nnnnnnnnnn nn                    52
```

APTAMER SELECTION METHOD

This application is the U.S. National Stage of International Application No. PCT/CA04/00482, filed Mar. 31, 2004, which claims benefit of U.S. Provisional applications Ser. No. 60/458,409 filed Mar. 31, 2003.

FIELD OF INVENTION

The present invention relates to a method for the in vitro selection of nucleic acid aptamers.

BACKGROUND OF THE INVENTION

DNA aptamers are single-stranded DNA molecules with defined tertiary structures for target binding. Aptamers recognize molecules other than nucleic acids with high affinity and specificity. Aptamers have been identified which can recognize a broad range of targets, including small molecules and large proteins. Aptamers can be produced synthetically and are very stable. They have the potential of being used as effective molecular tools for many applications including medical diagnosis, biosensing and drug screening.

One method for the selection of an aptamer that specifically binds to a target molecule is the SELEX process described in U.S. Pat. Nos. 5,475,096 and 5,270,163 (incorporated herein by reference). Briefly, the SELEX involves immobilizing a selected target on a column. A solution containing a library or assortment of random DNA or RNA molecules is contacted with the target under conditions that are favorable for binding. After a certain amount of time the column is flushed and those nucleotide molecules which bind to the target remain on the column. The unbound nucleic acid molecules will be eluted from the column. The nucleic acid-target complexes are then dissociated and the nucleic acid molecules that were selected by binding to the target are amplified. The cycle may be repeated to achieve a higher affinity nucleic acid.

In copending PCT application PCT/CA02/02007, which is incorporated herein by reference, the present inventors disclose a method for transforming a non-signaling aptamer into a fluorescent one based on the ability of aptamers to switch structure. In the absence of its cognate non-nucleic acid target, an aptamer forms a duplex structure with a complimentary nucleic acid molecule. In the presence of the target the nucleic acid duplex structure is dissociated and the aptamer assumes its tertiary structure.

Techniques that allow for the specific detection of molecules are highly sought after for the development of research and clinical tests. Thus, there remains a real need for more rapid and efficient methods for the identification and isolation of aptamers that are specific for particular targets.

SUMMARY OF THE INVENTION

An object of one aspect of the present invention is to provide novel strategies for aptamer selection and aptamer reporter engineering. A new methodology for creating effective signaling aptamers is provided as well as novel aptamers selected and engineered according to the methods of the invention.

As used herein, the term aptamer is used to refer to a nucleic acid molecule or oligonucleotide sequence that binds to a specific target. In general, aptamers may be DNA or RNA. They may be single stranded or double stranded and they may include nucleotide derivatives.

The present invention provides a general method for the exhaustive isolation of novel aptamer sequences by incorporating a structure switching selection step.

In one aspect, the present invention provides a method for selecting an aptamer cable of binding to a target. The method comprising the steps of i) interacting an antisense oligonucleotide with a library oligonucleotide having a complementary antisense binding domain to form a double stranded duplex, said library oligonucleotide further having a random nucleotide domain; ii) immobilizing the duplex structure on a solid support; iii) incubating the duplex structure in the presence of the target; and iv) collecting library oligonucleotides that dissociate from the duplex structure and bind to the target. The method may further comprise amplifying the library nucleotides collected at step iv) to provide an amplified population and sequencing clones derived from the amplified population. In another embodiment the method comprises providing a library oligonucleotide, said library oligonucleotide comprising an antisense binding domain, at least one random sequence domain, a 3' primer binding domain and a 5' primer binding domain; hybridizing the library oligonucleotide to a biotinylated antisense oligonucleotide to form a duplex molecule; interacting the duplex molecule with avidin coated beads to immobilize the duplex molecule on the beads; incubating the beads with the target; collecting oligonucleotides which have bound to the target; and amplifying the collected oligonucleotides.

In another aspect of the invention there is provided an aptamer comprising a sequence selected from the group consisting of SEQ. ID. NO. 6, SEQ. ID. NO. 7, SEQ. ID. NO. 8, SEQ. ID. NO. 9, SEQ. ID. NO. 10, SEQ. ID. NO. 11, SEQ. ID. NO. 12, SEQ. ID. NO. 13, SEQ. ID. NO. 14, SEQ. ID. NO. 15, SEQ. ID. NO. 16, SEQ. ID. NO. 17, SEQ. ID. NO. 18, SEQ. ID. NO. 19, SEQ. ID. NO. 20, SEQ. ID. NO. 21, SEQ. ID. NO. 22, SEQ. ID. NO. 23, SEQ. ID. NO. 24, SEQ. ID. NO. 25 and SEQ. ID. NO. 26. In one aspect of the invention, the aptamer is capable of binding to ATP and comprises a sequence selected from the group consisting of: SEQ. ID. NO. 6, SEQ. ID. NO. 7, SEQ. ID. NO. 8, SEQ. ID. NO. 9, SEQ. ID. NO. 10, SEQ. ID. NO. 11, SEQ. ID. NO. 12, SEQ. ID. NO. 13, SEQ. ID. NO. 14, SEQ. ID. NO. 20, SEQ. ID. NO. 21, SEQ. ID. NO. 22 and SEQ. ID. NO. 23. In another aspect, the aptamer is capable of binding to GTP and comprises a sequence selected from the group consisting of: SEQ. ID. NO. 15, SEQ. ID. NO. 16, SEQ. ID. NO. 17, SEQ. ID. NO. 18, SEQ. ID. NO. 19, SEQ. ID. NO. 24, SEQ. ID. NO. 25 and SEQ. ID. NO. 26.

In yet another aspect of the invention, a signaling structure switching aptamer complex is provided which comprises a sequence selected from the group consisting of: SEQ. ID. NO. 6, SEQ. ID. NO. 7, SEQ. ID. NO. 8, SEQ. ID. NO. 9, SEQ. ID. NO. 10, SEQ. ID. NO. 11, SEQ. ID. NO. 12, SEQ. ID. NO. 13, SEQ. ID. NO. 14, SEQ. ID. NO. 15, SEQ. ID. NO. 16, SEQ. ID. NO. 17, SEQ. ID. NO. 18, SEQ. ID. NO. 19, SEQ. ID. NO. 20, SEQ. ID. NO. 21, SEQ. ID. NO. 22, SEQ. ID. NO. 23, SEQ. ID. NO. 24, SEQ. ID. NO. 25 and SEQ. ID. NO. 26.

In a further aspect of the invention, there is provided an aptamer selection system. The selection system may be provided in the form of a kit. The selection system comprises an antisense oligonucleotide and a library oligonucleotide. The library oligonucleotide comprises an antisense binding domain having a sequence complementary to the antisense oligonucleotide and at least one random nucleotide domain. The antisense oligonucleotide is adapted to be attached to a solid support. The aptamer selection system/kit comprises a library oligonucleotide having a first primer binding domain at the 5' end and a second primer binding domain at the 3' end and the system/kit further comprises a first primer capable of binding to the first primer binding domain and a second primer capable of binding to the second primer binding domain. In a preferred embodiment, the library oligonucleotide comprises two random domains flanking the antisense binding domain. In another preferred embodiment, the antisense oligonucleotide is biotinylated and avidin-coated agarose beads are provided. In another preferred embodiment, the aptamer selection system includes an antisense oligonucleotide comprising SEQ.ID. No. 1, a library oligonucleotide comprising SEQ.ID.NO. 2, a P1 oligonucleotide comprising SEQ.ID.NO.3, a P2 oligonucleotide comprising SEQ.ID.NO. 4 and a P3 oligonucleotide comprising SEQ.ID.NO.5.

DETAILED DESCRIPTION

The present invention provides a novel in vitro method for the selection of aptamers based on the ability of an aptamer to switch from a linear/duplex structure to a tertiary structure. The method provides a means to directly select aptamers for a broad range of targets. The selected aptamers may be converted to structure-switching signaling aptamers.

The invention is based on the working principle of structure-switching aptamers. In the absence of its cognate target, an aptamer sequence can form a duplex structure with a complimentary nucleic acid sequence. In the presence of target, the duplex structure will dissociate and the aptamer will switch to its tertiary structure. It has previously been demonstrated that aptamer sequences can be converted into signaling aptamers based on this concept.

In the present invention, this structure switching mechanism can be used to select novel aptamer sequences. An entire DNA library is "trapped" through DNA hybridization and the target is used as a "bait" to release the potential aptamers from the trap. In other words, the aptamer sequence switches from a duplex structure (DNA hybridization) to its tertiary structure when the target (bait) is introduced.

The method of the present invention involves the use of a library of oligonucleotides comprising at least one random domain and an antisense binding domain. The library oligonucleotide is hybridized to an anchored antisense oligonucleotide through the antisense binding domain to form a duplex structure. When an appropriate target to which the random domain can bind is introduced, the library oligonucleotide will form a tertiary structure with the target. The strength of this interaction will force the duplex structure apart and the oligonucleotide will be released from the anchored or immobilized antisense molecule. The selected aptamer DNA can then be converted into a signaling structure switching aptamer as previously described.

In one preferred embodiment, illustrated in FIG. 1, the library oligonucleotide comprises two random domains, one on each side of the antisense binding domain. This arrangement facilitates the selection of aptamer sequences which will be useful in the development of good structure-switching aptamers. In this embodiment, a selection system 10 is provided which comprises a DNA library oligonucleotide 12 and an immobilized antisense oligonucleotide 14. The DNA library oligonucleotide typically comprises, in order, a first primer binding domain 16, a first random domain 18, an antisense-binding domain 20, a second random domain 22 and a second primer binding domain 24. The order is not essential, however, the positioning of the antisense binding domain between the random domains ensures that the selected aptamers can be easily converted into signaling structure switching aptamers.

Figure 1A:
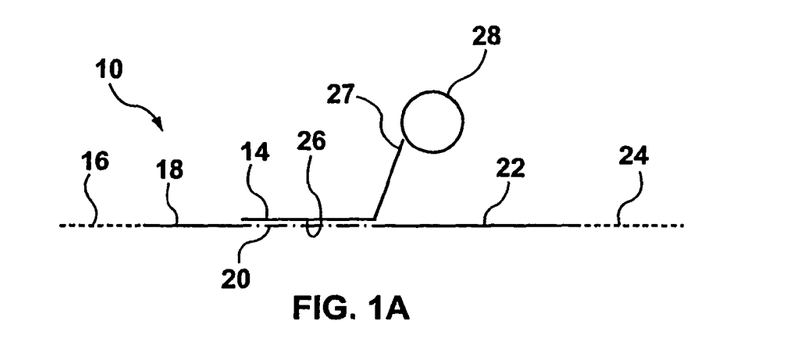
FIG. 1A is a schematic illustration of a selection system according to one aspect of the invention in the absence of target.

In the absence of the target as shown in FIG. 1, the antisense binding domain 20 forms a duplex structure 26 with the biotinylated antisense DNA 14 that is immobilized on avidin coated agarose beads 28. This duplex structure is shown in FIG. 1A. The density of antisense DNA is preferably sufficient to bind all the library DNA molecules so that there are no free library DNA molecules left in solution. While a biotin-avidin immobilization scheme is referred to for illustrative purposes, it is clearly apparent that other methods could also be used to separate bound (i.e. duplex forming) and unbound (non-duplex forming) oligonucleotides.

Figure 1B:
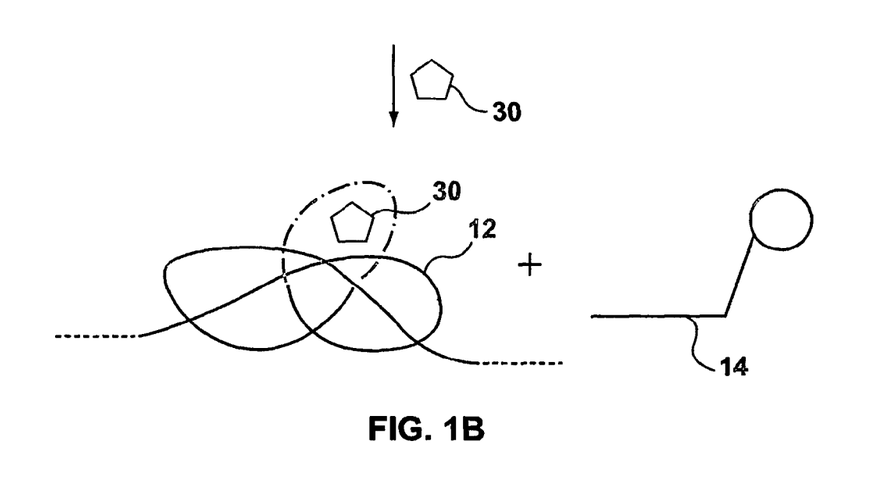
FIG. 1B illustrates the selection system of FIG. 1A in the presence of a target.

Referring now to FIG. 1B, when the target 30 is present, only those oligonucleotide library molecules 12 which specifically bind the target will switch structure from the immobilized duplex state to a ligand-complex state. The dissociation of the duplex state, when the aptamer switches to its tertiary target binding structure, results in the release of the aptamer/target complex 32 from the agarose beads 28. The aptamer molecules which are now in solution can be isolated and further manipulated.

Figure 1C:
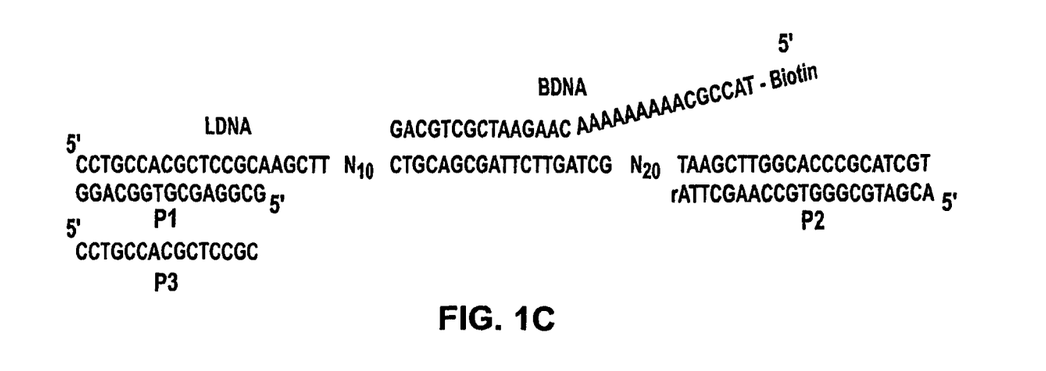
FIG. 1C illustrates the nucleotide components that comprise one embodiment of the selection system of the present invention, the BDNA, LDNA, P1, P2, and P3 oligonucleotides shown therein having the nucleotide sequences of SEQ ID NOs:1-5, respectively.

FIG. 1C illustrates one example of the construction of a selection system according to the present invention. These sequences are provided merely for illustrative purposes and are not intended to limit the scope of the invention. It is clearly apparent to one skilled in the art that other pairs of complementary sequences could also be used. In this illustration, the library oligonucleotide (LDNA) is 91 nucleotides long and contains a primer binding domain at the 3' end and at the 5' end. The library oligonucleotide corresponds to SEQ.ID.NO. 2. Each molecule in the library contains a central, 15-nt region that can hybridize with an antisense DNA used as the capture sequence to immobilize the library onto a solid support. Two random-sequence regions of 10 nt and 20 nt, $N_{10}$ and $N_{20}$, respectively, were designed to flank the antisense DNA binding domain. The lengths of each of the random regions can be varied as desired. The two random-sequence domains are further flanked by constant, primer-binding regions (21 and 15 nt at the 5'-end and 3'-end, respectively). A 30-nt DNA (denoted BDNA) with a biotin moiety at its 5' end is used as the antisense DNA. BDNA corresponds to SEQ.ID.NO1. The biotin moiety enables the immobilization of the BDNA onto avidin-coated agarose beads. The 15-nt stretch at the 3'-end of the BDNA is designed to form a 15-bp duplex structure with the central, antisense binding domain of the LDNA. The primer binding domains are blocked by complementary oligonucleotides to prevent their involvement in the binding site of the aptamers. Primer P1 (SEQ.ID.NO. 3) blocks the 5' binding domain and primer P2 (SEQ.ID.NO. 4) blocks the 3' binding domain. Additional P2 primer and a P3 primer (SEQ.ID.NO. 5) are provided for subsequent PCR amplification of selected sequences.

Figure 2:
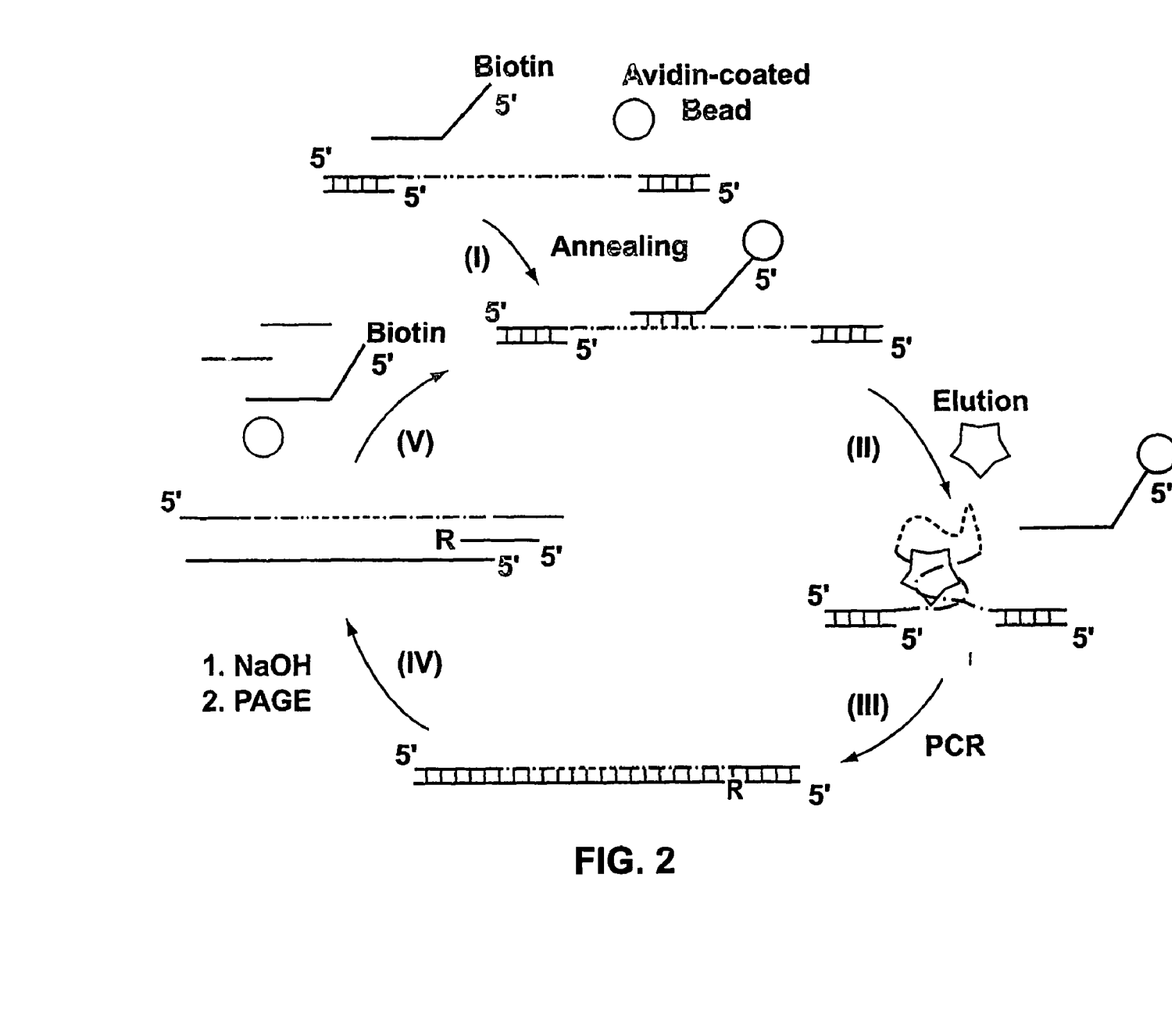
FIG. 2 is a schematic illustrating one embodiment of an aptamer selection method according to the present invention.

FIG. 2 illustrates how the aptamer selection method of the present invention can be used to identify and amplify aptamer sequences. Referring to Step I, LDNA and BDNA oligonucleotides are annealed in selection buffer. The primer binding domains may be optionally blocked with P1 and P2 to prevent their potential involvement in target binding. Once the hybridization is complete, the duplex molecules are mixed with the avidin coated beads for a sufficient time for the biotin to interact with the avidin. The avidin coated beads are preferably arranged in a column. The immobilized LDNA-BDNA-P1-P2 assembly is washed repeatedly with the selection buffer to eliminate any LDNA molecules which have not formed a strong duplex with the BDNA. In a variation of the method, the antisense DNA is mixed with the avidin coated beads and then interacted with the library. It is also apparent that the avidin could be immobilized on other supports besides agarose beads and that the beads can be separated from solution by other means, such as centrifugation, magnetization, etc. Other immobilization systems, known to those skilled in the art can also be used.

In step II, the immobilized DNA on the beads is incubated with a selected target for a predetermined amount of time, typically about one hour. The oligonucleotides which bind to the target are thereby released into solution by the structure-switching mechanism. In step III, these molecules are collected and amplified by polymerase chain reaction (PCR) using P2 (a ribonucleotide-terminated primer) and P3 as primers. At step IV, the double-stranded DNA product is digested with, for example, 0.2 M NaOH at 90° C. for 10 minutes to cleave the ribonucleotide linkage. The digested DNA is subjected to 10% denaturing polyacrylamide gel electrophoresis (PAGE) to isolate the single-stranded DNA molecules corresponding to the size of the original DNA library. The isolated DNA molecules are then subjected to a new round of selection.

Multiple rounds can be done to enhance the specificity and the affinity of the aptamer sequence. Furthermore, by adjusting the sequence of the antisense sequence so that the strength of the duplex structure is varied, the affinity of the aptamer sequence can be controlled.

Figure 3:
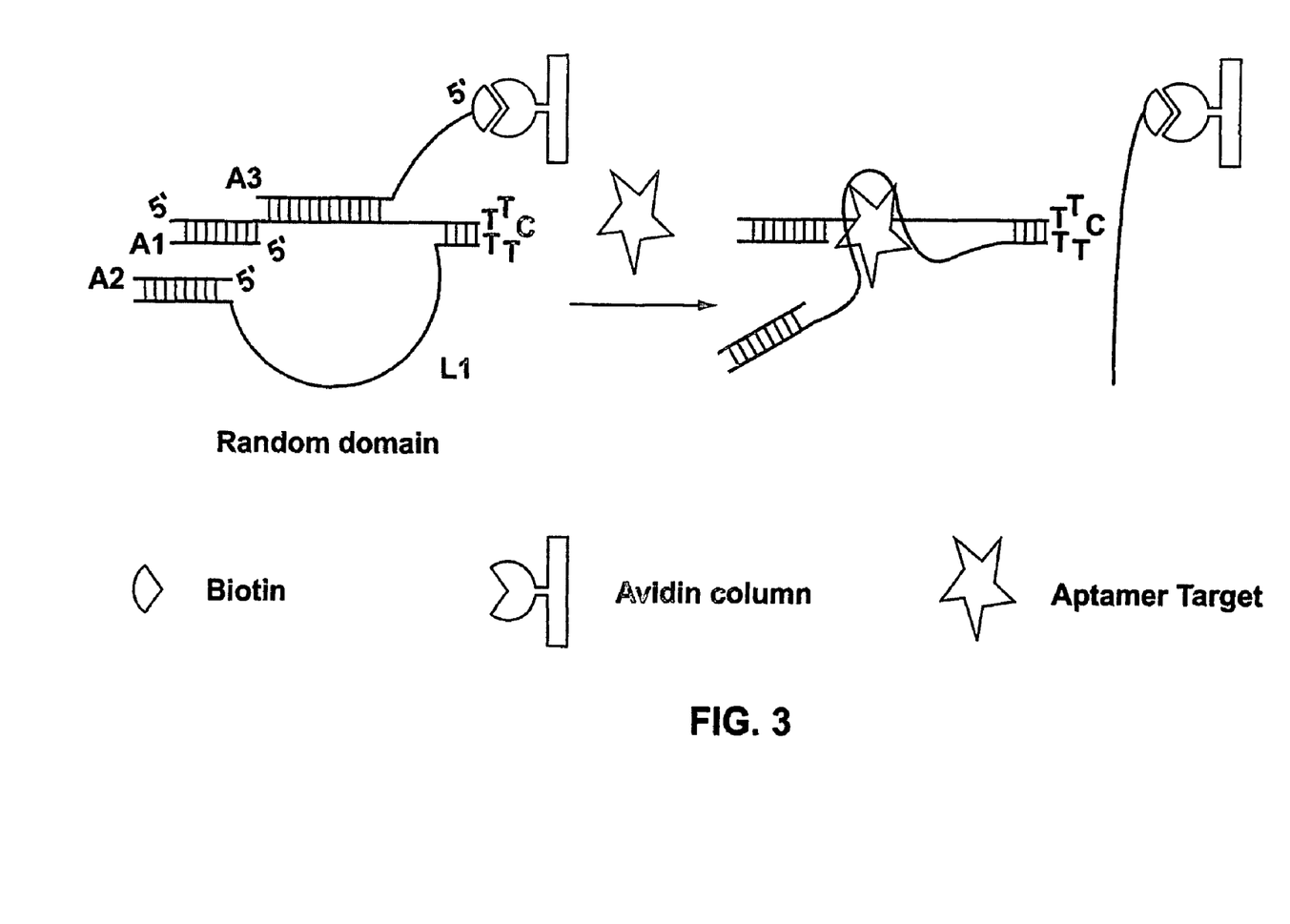
FIG. 3 is a schematic representing another embodiment of an aptamer selection method according to the present invention.

Another preferred embodiment is shown in FIG. 3. In this embodiment, several DNA molecules are used. The library DNA is termed L1. The library oligonucleotide may optionally include regions of internal complementarity to form an internal duplex as shown at the right in FIG. 3. Two short oligonucleotides termed A1 and A2 hybridize to the 5' and 3' ends, respectively, of the library oligonucleotide. Another short oligonucleotide, termed A3, is an antisense oligonucleotide. A3 has a binding sequence which is complimentary to a segment of the library oligonucleotide, a linker region and a biotin at the 5' end for immobilizing the complex onto an avidin column. As shown in FIG. 3, the antisense hybridizes with the library DNA and immobilizes it on the avidin column. When a particular target is introduced, those library oligonucleotides that contain an aptamer sequence specific for that target will dissociate from the column as they change structure to bind to the target.

The selection process comprises the following steps:
a. hybridization of library oligonucleotides to biotinylated antisense oligonucleotides to form DNA duplexes;
b. loading the resulting DNA duplexes onto an avidin column;
c. introducing a target molecule;
d. eluting the oligonucleotide/target complex;
e. amplifying the eluted oligonucleotide by PCR; and
f. generating single-stranded DNA molecules to be used for a new round of selection.

The utility of the aptamer selection method of the present invention was illustrated by using the method to select several aptamers that are specific for certain NTPs. The specific selection process is described more fully in the examples below and the results of the selection method are illustrated with reference to FIGS. 4 to 8.

The present invention also provides aptamers identified and selected by the method of the invention. Several novel aptamers were identified, cloned and sequenced using the above-described method for the selection of aptamers. Several ATP specific and GTP-specific aptamers were selected. These aptamers were shown to be target specific and then sequenced.

Figure 4:
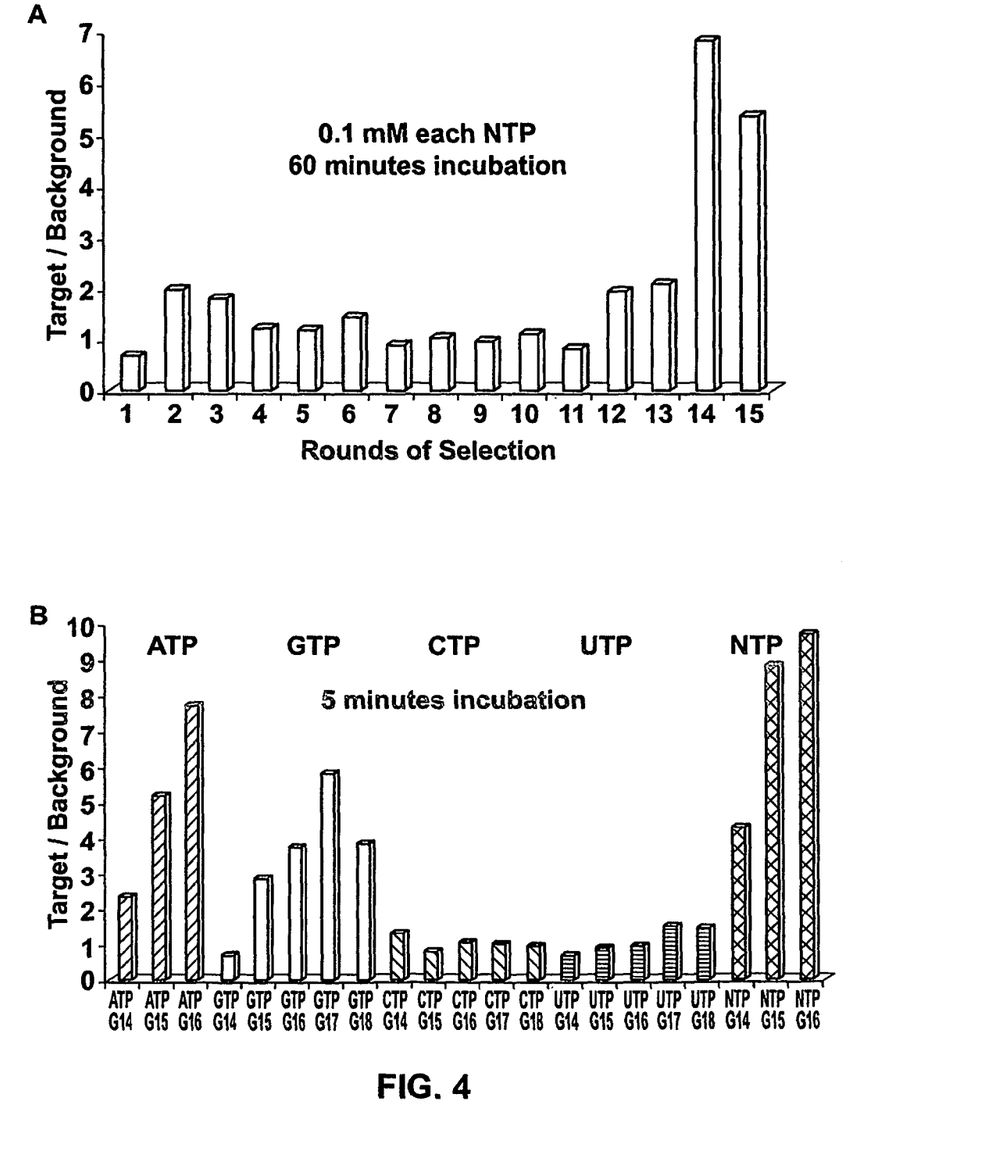
FIG. 4A shows the selection progress through several rounds of selection using a pool of NTPs.
FIG. 4B demonstrates the results from several rounds of selection with specific NTPs.

FIG. 4 demonstrates the in vitro selection progress for these aptamers. After 14 rounds of selection using a pool of combined NTPs, the G15 population was divided into five pools for parallel selection for ATP, GTP, CTP, UTP and NTP. The results indicate that there was a significant enrichment of ATP and GTP binding aptamers.

Figure 5:
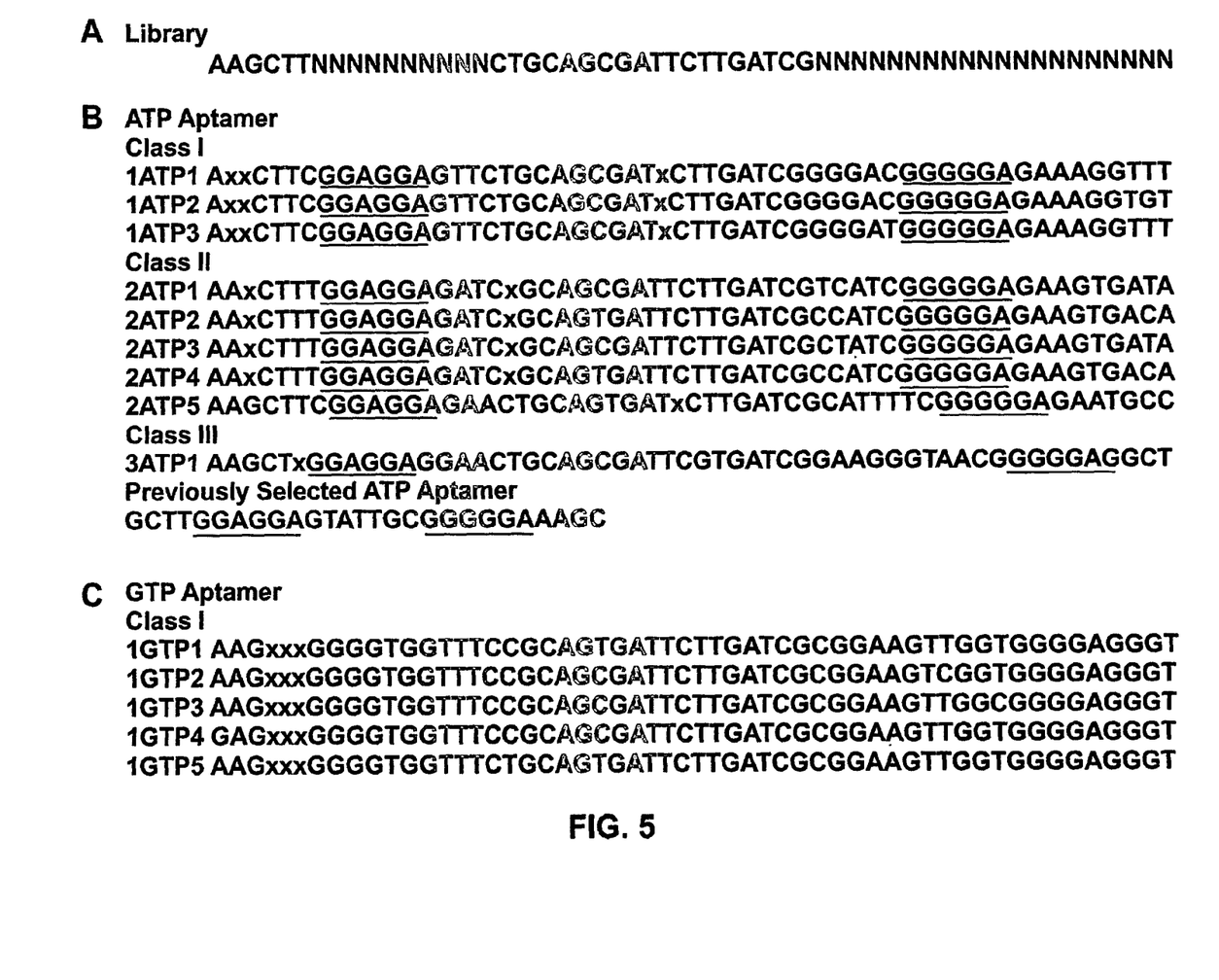
FIG. 5A illustrates a library sequence (SEQ ID NO:27) used in the aptamer selection method.
FIG. 5B illustrates the sequences of several anti-ATP aptamers selected according to the method of the present invention; more specifically, ATP Aptamers 1ATP1-3, 2ATP1-5, and 3ATP1 shown in this figure have the nucleotide sequences of SEQ ID NOs:6-14, respectively.
FIG. 5C illustrates the sequences of several anti-GTP aptamers; i.e., 1GTP1-5 having the nucleotide sequences of SEQ ID NOs:15-19.

Using the enriched populations several ATP and GTP specific aptamers were cloned and sequenced. The selection and cloning are described more fully in the Examples below. The sequences are shown in FIG. 5 and described in the attached sequence listing as SEQ.ID. NOS. 6 to 19.

Figure 6:
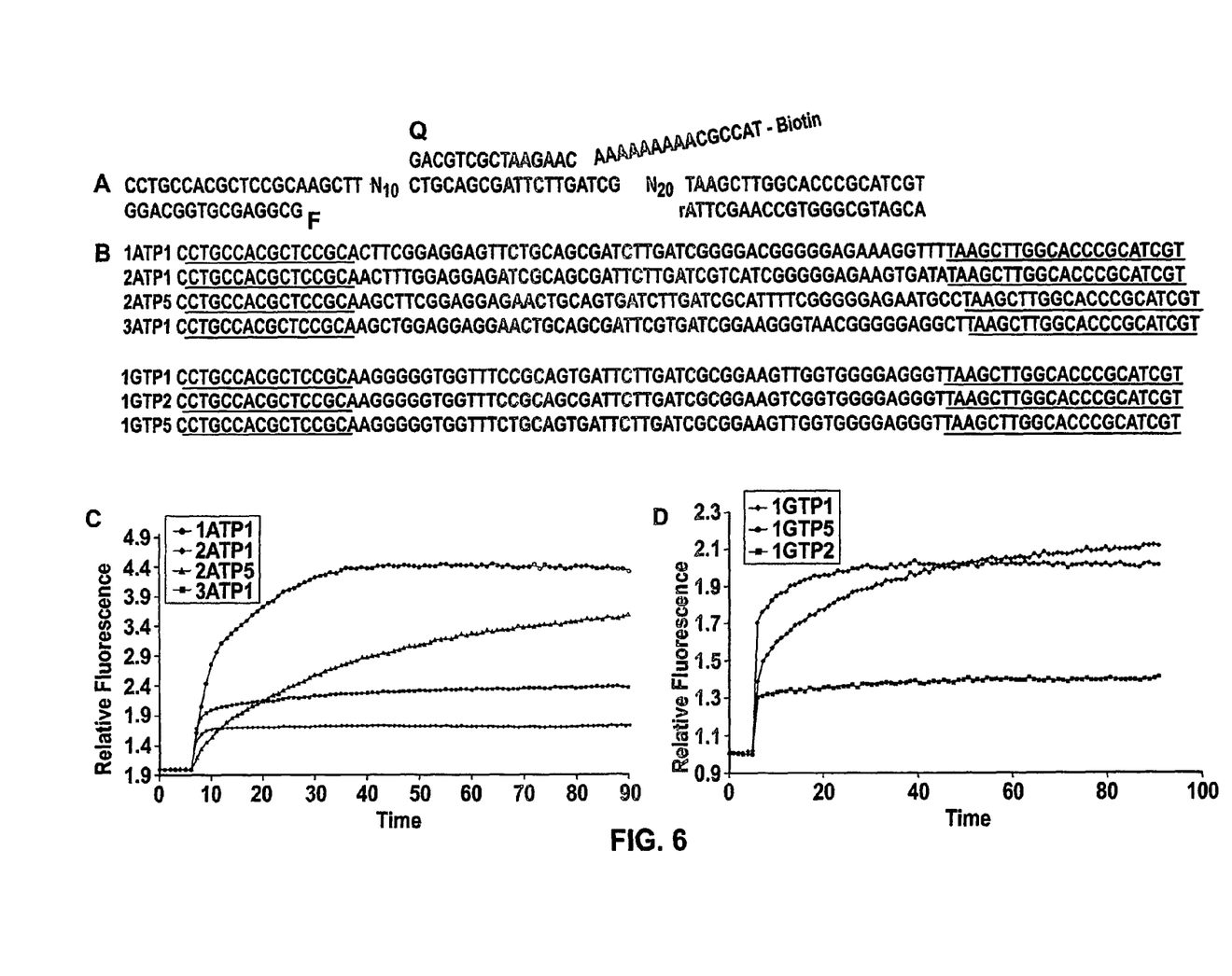
FIG. 6A illustrates the oligonucleotide assembly structure used for selection of signaling aptamers; the oligonucleotides in this figure have the same nucleotide sequences as the counterparts in FIG. 1C.
FIG. 6B illustrates the sequences of severn chosen ATP and GTP aptamer sequences including primer binding domains. Aptamers 1ATP1, 2ATP1, 2ATP5, 3ATP1, 1GTP1, 1GTP2, and 1GTP5 have the nucleotide sequences of SEQ ID NOs: 20-26, respectively.
FIG. 6C illustrates the signaling profiles for the ATP aptamers.
FIG. 6D illustrates the signaling profiles for the GTP aptamers.
Figure 7:
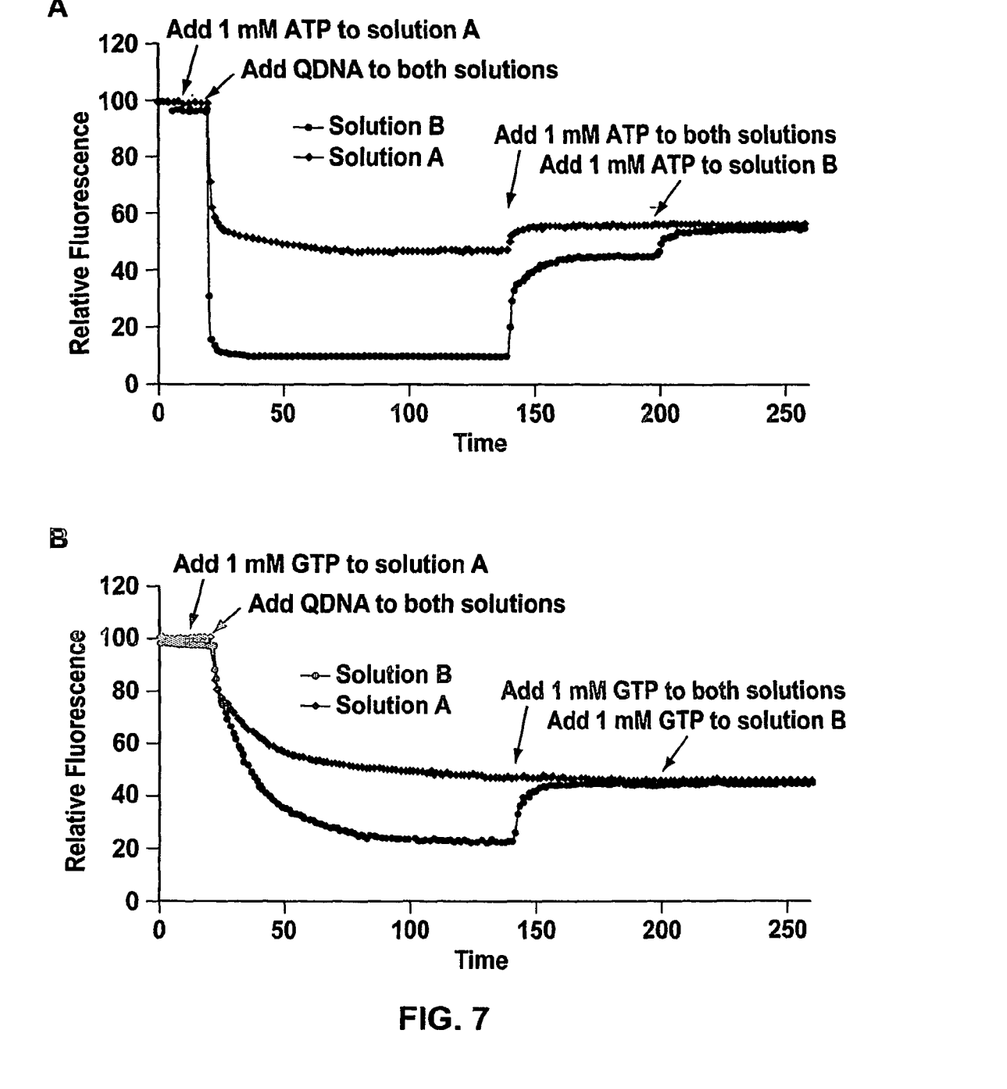
FIG. 7A demonstrates structure switching of 1ATP1 as a representative anti-ATP aptamer.
FIG. 7B demonstrates structure switching of GTP2 as a representative anti-GTP aptamer.

The present invention also provides novel signaling aptamer complexes derived from the selected aptamer sequences. The sequences of seven chosen signaling ATP and GTP aptamers including primer binding domains are shown in FIG. 6 and are described as SEQ.ID.NOS. 20 to 26. These aptamers can be converted into signaling aptamer complexes. The methods for the preparation of the signaling structure switching aptamers is described more fully in Example 3 below. These aptamers have excellent structure switching signaling capabilities as illustrated in FIGS. 6C and 6D.

Figure 8:
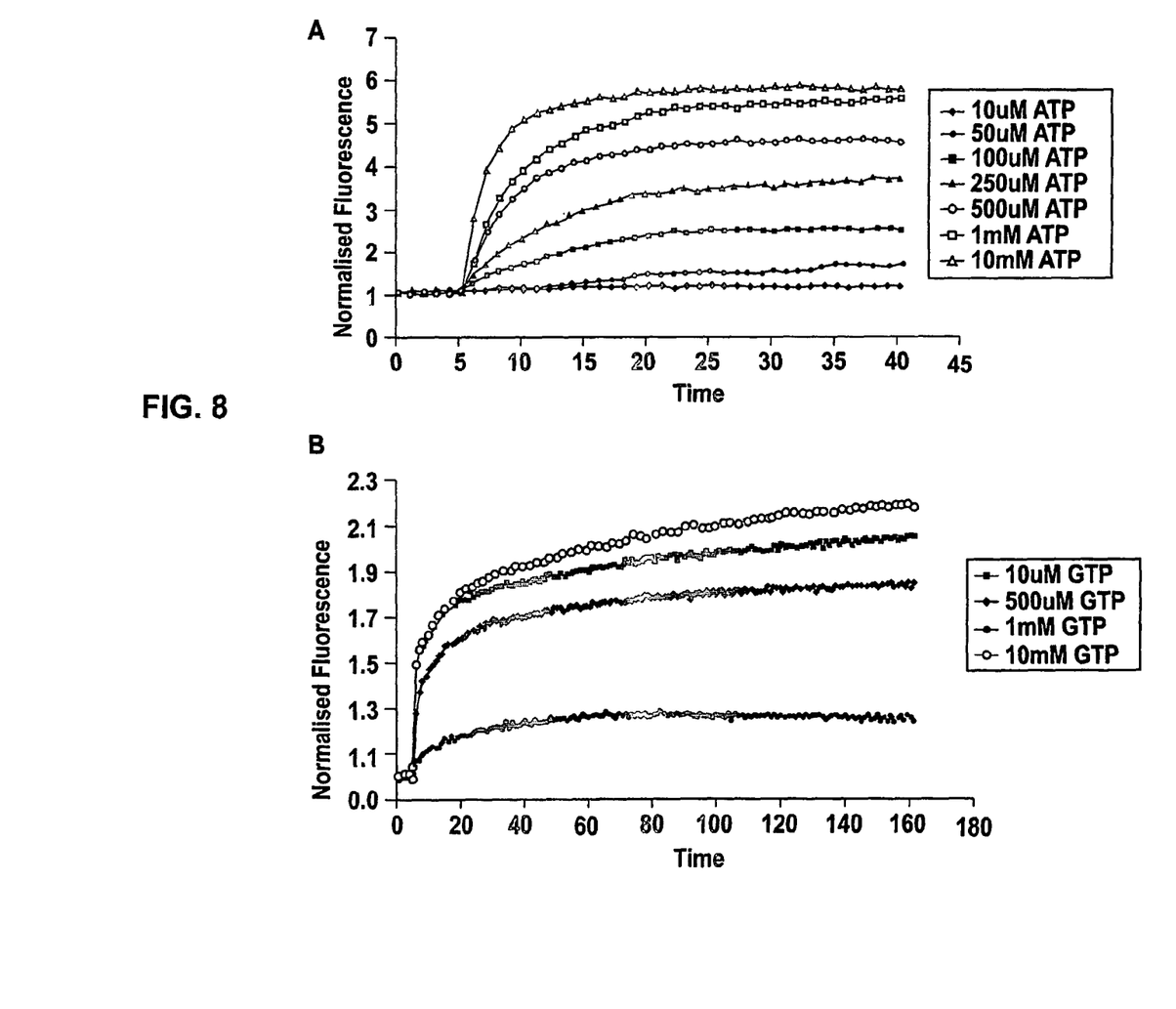
FIG. 8A shows the signal generated by 1ATP1 in response to the concentration of the target, ATP.
FIG. 8B shows the signal generated by 1GTP2 in response to the concentration of the target, 1GTP2.

The signaling aptamers of the present invention were shown to be target specific (FIG. 7) and to react in a dose dependant manner (FIG. 8). Specifics of these experiments are detailed in the Examples below.

The present invention also provides an aptamer selection system or kit. The system can be used using components derived from different sources or the components of the system may be provided as a kit. The kit or system comprises an antisense oligonucleotide and a library oligonucleotide as described above. The library oligonucleotide has one or more regions where random sequences can be inserted. The length of the random domains may vary. The antisense oligonucleotide is adapted to be anchored to a solid support in some way so that when a duplex is formed between the antisense oligonucleotide and the antisense binding domain of the library nucleotide, the duplex is immobilized. The system also involves primers capable of binding to the primer binding domains of the library oligonucleotide for PCR amplification. The primers may be included in the kit or a user may wish to use their own primers to insert desired sequences.

The method of present invention provides significant advantages over prior art methods for the selection of aptamers. Prior art methods that involve the immobilization of the target on a column are expensive and require a new set-up to screen for each potential target. In the method of the present invention an oligonucleotide library is immobilized through duplex formation. The same library can be used to screen for aptamers specific to different targets. In addition, DNA is relatively cheap and easy to make, yet demonstrates high specificity.

The present method also provides a way to select aptamers based on a level of affinity. The competition between the binding of the LDNA to the immobilized BDNA (duplex formation) and the binding of the LDNA to a target (the formation of the tertiary complex), allows for precise control of aptamer affinities. For example, if there is a strong LDNA-BDNA duplex, the aptamer sequence must have a very high affinity for the target to break the duplex to elute the aptamer from the trap. Although methods exist in the literature for the creation of various aptamers from random-sequence DNA libraries, no approach has yet been able to provide good control over the affinity of the resulting aptamers. Therefore, the use of the structure-switching mechanism for in vitro selection should offer a significant advantage in this regard. In addition, the selection method is applicable to essentially all biological targets as long as they are soluble in aqueous solution, regardless of their size, physical nature and chemical trait. Furthermore, the aptamers selected by this method can be directly converted into signaling aptamers as fluorescent reporters for biological detection since they have demonstrated an ability to structure switch. Thus, the present invention significantly advances the practical application of aptamers as useful molecular tools to study biological systems.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention. Methods of molecular biology not specifically described are well known to those skilled in the art.

Example 1

Selection of NTP Specific Aptamers

LDNA, BDNA, P1 and P2 oligonucleotides were first annealed in selection buffer and then mixed with avidin-agarose beads. The immobilized LDNA-BDNA-P1-P2 assembly was washed repeatedly with the selection buffer to eliminate the LDNA molecules incapable of tight binding to BDNA. Next, the beads were eluted with a mixture of ATP, GTP, CTP and UTP at 0.1 mM each (final concentration) for one hour. The molecules capable of binding to one of the NTPs and releasing themselves into solution by the structure-switching mechanism were collected and amplified by polymerase chain reaction (PCR) using P2 (a ribonucleotide-terminated primer) and P3 as primers. The double-stranded DNA product was digested with 0.2 M NaOH at 90° C. for 10 minutes to cleave the ribonucleotide linkage. Finally, the digested DNA was subjected to 10% denaturing polyacrylamide gel electrophoresis (PAGE) to isolate the single-stranded DNA molecules corresponding to the size of the original DNA library. Thus purified DNA molecules were subjected to a new round of selection.

The progression of the in vitro selection experiment is illustrated in FIG. 4A. The y-axis represents the ratio (denoted "target/Background") of the fraction of DNA released by the addition of NTPs over the fraction of DNA released in the selection buffer only (for the same incubation time). After 14 rounds of selection, the Target/Background ratio increased 7-fold (FIG. 4A). Tests using individual NTPs as the eluting target revealed that the G14 generation was mainly responsive to ATP and had no significant switching capability in the presence of GTP, CTP or UTP. At this point, the selected pool was split into four subpools, each of which was subjected to additional rounds of selection using a single NTP as the eluting target. After two more rounds of selection (G16) 20% of ATP pool was switched from the column to solution in 5 minutes, representing an 8-fold increase over the background. Similar observations were seen with the GTP selection. In contrast, no significant enrichment was observed for the CTP and UTP selection after five more rounds of selection after the pool-splitting. This data suggest that the anti-CTP and anti-UTP specific structure-switching aptamers were far less abundant in the original pool and were not as competitive as anti-ATP and anti-GTP aptamers.

Example 2

Cloning and Sequencing of ATP and GTP Specific Aptamers

G16 population from ATP and G18 population from GTP selections were cloned and sequenced (FIG. 5). Three sequence classes, denoted 1ATP, 2ATP and 3ATP, were identified from the ATP pool (FIG. 5B). Only one sequence class was seen from the GTP pool (FIG. 5C). It is interesting that all anti-ATP classes contain two sequence domains (FIG. 5B, underlined) that are found in the sequence of a previously isolated anti-ATP DNA aptamer (FIG. 5C, bottom). These data suggest that the same ATP-binding elements are isolated from two independent in vitro selection experiments with completely different selection strategies.

Example 3

Preparation of Signaling Structure-Switching Aptamers

To test the target-binding ability of these aptamers and their signaling capabilities, four sequences from the ATP pool and three sequences from the GTP binding pool were chemically synthesised (FIG. 6B). A P1 oligonucleotide that was labeled with a fluorescein at its 5' end (the P1 is now termed FDNA) and the BDNA with DABCYL as the quencher at its 3' end (the BDNA is now termed QDNA) were used. By mixing P2, FDNA and QDNA with each of the candidate aptamer, a duplex assembly is formed that brings the fluorophore and the quencher into close proximity to render a low level of fluorescence. The solutions containing the aptamer assembly were incubated for 5 minutes and then 1 mM of ATP, and GTP respectively (at minute 5) were added. All the signaling aptamers responded to the addition of the target (FIGS. 6C and 6D) by switching the duplex structure to the complex tertiary structure. The two best signaling reporters, one each from the ATP selection and the GTP selection (i.e., 1ATP1 and 1GTP2) were chosen for additional testing.

To further confirm the structure-switching capability of the aptamers, an experiment was conducted using two aptamer-containing solutions (solutions A and B) for each candidate aptamer (FIG. 7A for 1ATP1 and FIG. 7B for 1GTP2). In the experiment using the anti-ATP aptamer 1ATP1, for both solutions A and B, FDNA, P2 and 1ATP1 were incubated for 10 min in the absence of both QDNA and ATP. Because of the lack of QDNA, the fluorescence intensity of each solution was at its highest. At $11^{th}$ minute, 1 mM ATP was added to solution A while no ATP was added to solution B. From the observation that both solutions A and B maintained the same level of fluorescence intensity, it is apparent that the addition of ATP did not alter the fluorescence intensity of the solution. Each mixture was further incubated for 10 min and at the $11^{th}$ minute, QDNA was added to both solutions. The fluorescence intensity of both solutions decreased. However, the fluorescence intensity of the target-containing solution (solution A) was significantly higher than the target-lacking solution (solution B). The data are consistent with the formation of the aptamer-ATP complex in solution A and reduced amount of the QDNA-aptamer duplex structure in solution A in comparison to solution B. At $140^{th}$ min, 1 mM ATP was added to each solution. For solution A, only a small increase of fluorescence intensity was observed, suggesting that the aptamer's target-binding site was largely saturated prior to the addition of the extra ATP. In contrast, a significant fluorescence intensity increase was observed upon the target addition to solution B, indicating the structure-switching from the aptamer-QDNA duplex to the aptamer-ATP complex. Finally, when additional 1 mM ATP was added to the solution B (therefore both solutions A and B contained exact concentrations of ATP and DNA species), solution B reached the same level of fluorescence observed for solution A. The same level of fluorescence reached by both solutions in the end with different orders of ATP and QDNA additions indicates that the switching between the duplex structure and the complex structure is an equilibrium process. A similar experiment was performed with the anti-GTP aptamer and the observations were very similar (FIG. 7B).

Example 4

Dose Responsiveness of the Aptamers

The aptamers were assessed for their response to different concentrations of the target (FIG. 8). The 1ATP1 or 1GTP2 assembly described in FIG. 6A, were incubated for 5 minutes in the absence of ATP or GTP. Different concentrations of each target was then added ranging from 10 μM to 10 mM. Both aptamers showed fluorescence intensity increases in a concentration dependant manner, indicating that they could be used for quantitation of their cognate ligands.

Example 5

Detailed Methodology of Aptamer Selection, Cloning and Characterization

Both standard and modified DNA oligonucleotides were prepared by automated DNA synthesis using cyanoethyl-phosphoramidite chemistry (Keck Biotechnology Resource Laboratory, Yale University; Central Facility, McMaster University). 5'-Fluorescein and 3'-DABCYL (4-(4-dimethylamino-phenylazo)benzoic acid) moieties (in FDNA and QDNA, respectively) were introduced using 5'-fluorescein phosphoramidite and 3'-DABCYL-derivatized controlled pore glass (CPG) (Glen Research, Sterling, Va.) and were purified by reverse phase HPLC. HPLC separation was performed on a Beckman-Coulter HPLC System Gold with a 168 Diode Array detector. The HPLC column was an Agilent Zorbax ODS C18 Column, with dimensions of 4.5 mm×250 mm and a 5-□m bead diameter. A two-solvent system was used for the purification of all DNA species, with solvent A being 0.1 M triethylammonium acetate (TEAA, pH 6.5) and solvent B being 100% acetonitrile. The best separation results were achieved by a non-linear elution gradient (10% B for 10 min, 10% B to 40% B over 65 min) at a flow rate of 0.5 mL/min. It was found that the main peak had very strong absorption at both 260 nm and 491 nm. The DNA within ⅔ of the peak-width was collected and dried under vacuum. Unmodified DNA oligonucleotides were purified by 10% preparative denaturing (8 M urea) polyacrylamide gel electrophoresis (PAGE), followed by elution and ethanol precipitation. Purified oligonucleotides were dissolved in water and their concentrations were determined spectroscopically.

Nucleotides (100 mM stocks) were purchased from MBI-Fermentas. All other chemical reagents were obtained from Sigma.

For the first round of in vitro selection experiments, 2000 pmol of LDNA, 10000 pmol of BDNA and 2500 pmol each of P1 and P2 were incubated in selection buffer (1× SB; 300 mM NaCl, 50 mM KCl, 10 mM $MgCl_2$ and 50 mM Tris.HCl pH 8.3) at 4° C. for overnight. This mixture was then incubated with 200 μL of avidin-coated agarose beads (pre-washed several times with 1× SB) for 45 minutes at room temperature. The supernatant was then removed from the beads, which were subsequently washed for five more times with 200 μL of 1× SB. The last wash was one hour (same duration as the target incubation), in order to have an estimate for the background. We then added the target (a mixture of ATP, CTP, GTP and UTP each at a final concentration of 0.1 mM) to the beads. The selection was monitored by the calculating ratio the radioactivity found in the target-containing solution and that in the solution from the last wash (background). The DNA molecules in the initial library was phosphorylated with polynucleotide kinase and [γ-$^{32}$P]ATP. The DNA found in the target-containing solution was amplified by PCR with the ribo-terminated primer P2 and a normal DNA primer P3. The double-stranded DNA product obtained was treated with 90 μl of 0.25 M NaOH at 90° C. for 10 min before neutralized by the addition of 10 μl of 3 M NaOAc (pH 5.5). The DNA species were precipitated by ethanol, purified on PAGE to obtain the sense strand for the next round of selection.

For the next 14 rounds of selection, the purified DNA population from the previous round was incubated with P1 and P2 (each in 1.5-fold excess), BDNA (in 5-fold excess). The DNA mixture was denatured at 90° C. for 3 minutes and annealed at room temperature for 30 minutes in 1× SB before mixed with 200 μl of avidin-coated agarose beads (pre-washed with SB) for 15 minutes. The avidin beads was washed at least 10 times with SB before eluted with the NTP mixture (0.1 mM each) for one hour. 1% of eluted solution was directly used the template for PCR amplification.

The populations were then assessed for specificity for specific NTPs. At 14 rounds of selection using combined NTPs as the target, the G15 population was split into five pools for 5 parallel selections, one for each individual NTP (ATP, GTP, CTP and UTP) and the other for the NTP mixture. In the same time, the target elution time was reduced to 5 minutes.

ATP and GTP specific aptamers were cloned and sequenced. DNA sequences from G18-ATP pool and G18-GTP pool were amplified by PCR and cloned into a vector by the TA cloning method. Plasmids containing individual catalysts were prepared using the Qiagen Mini-Prep Kit. DNA sequencing was performed on a CEQ 2000XL capillary DNA sequencer (Beckman-Coulter) following the manufacturer's recommended procedures.

The following general procedures were used for fluorescence measurements. The following concentrations of oligonucleotides were used for fluorescence measurements: 125 nM for FDNA, 250 nM for the selected aptamers, 375 nM for p2 and 1000 nM for the QDNA. The ratio of FDNA:MAP:QDNA:p2 was set to be 1:2:8:3 for simulating the best selection conditions. The assay buffer was similar to the selection buffer 1× SB. The fluorescence intensities were recorded on a Cary Eclipse Fluorescence Spectrophotometer (Varian) with excitation at 490 nm and emission at 520 nm. The sample volume in all cases was 50 μL.

We claim:

1. A method for selecting aptamer capable of binding to a target, said method comprising the steps of: i) interacting antisense oligonucleotide having the nucleotide sequence of SEQ ID NO: 1 and being adapted to be attached to a solid support with an oligonucleotide library containing multiple oligonucleotides, each of which includes an antisense binding domain having a sequence complementary to SEQ ID NO: 1 and a random nucleotide domain, wherein the antisense oligonucleotide and the oligonucleotides in the library form double stranded duplexes, ii) immobilizing the duplexes on a solid support; iii) incubating the duplexes in the presence of the target; and iv) collecting library oligonucleotides that dissociate from the duplexes and bind to the target.

2. The method of claim 1, further comprising amplifying the library oligonucleotides collected at step iv) to provide an amplified population.

3. The method of claim 2 further comprising the step of sequencing clones derived from the amplified population.

4. A method for the selection of an aptamer specific for a target, said method comprising the steps of: i) providing an oligonucleotide library containing multiple oligonucleotides, each of which includes an antisense binding domain having a sequence complementary to SEQ ID NO: 1, at least one random sequence domain, a 3' primer binding domain and a 5' primer binding domain; ii) hybridizing the oligonucleotides in the library to a biotinylated antisense oligonucleotide having the nucleotide sequence of SEQ ID NO:1 to form duplex molecules on beads; iii) incubating the beads of ii) with the target; iv) collecting oligonucleotides which have bound to the target; and v) amplifying the collected oligonucleotides.

5. An aptamer selection system comprising an antisense oligonucleotide having the nucleotide sequence of SEQ ID NO:1, and an oligonucleotide library containing multiple oligonucleotides, each of which includes an antisense binding domain having a sequence complementary to SEQ ID NO:1 and at least one random nucleotide domain, wherein said antisense oligonucleotide is adapted to be attached to a solid support.

6. The aptamer selection system according to claim 5, wherein each of the oligonucleotides in the library further comprises a first primer binding domain at the 5' end and a second primer binding domain at the 3' end.

7. The aptamer selection system according to claim 6, further comprising a first primer capable of binding to the first primer binding domain and a second primer capable of binding to the second primer binding domain.

8. The aptamer selection system according to claim 5, wherein each of the oligonucleotides in the library comprises two random domains flanking the antisense binding domain.

9. The aptamer selection system according to claim 5, wherein the antisense oligonucleotide is biotinylated.

10. The aptamer selection system according to claim 9, further comprising avidin agarose beads.

11. An aptamer selection system comprising an antisense oligonucleotide comprising SEQ ID. NO. 1, an oligonucleotide library containing multiple oligonucleotides each of which includes SEQ ID. NO. 2, a P1 oligonucleotide comprising SEQ ID. NO. 3, a P2 oligonucleotide comprising SEQ ID NO. NO. 4, and a P3 oligonucleotide comprising SEQ ID. NO. 5.

12. The aptamer selection system according to claim 6, wherein each of the oligonucleotides in the library comprises two random domains flanking the antisense binding domain.

13. The aptamer selection system according to claim 7, wherein each of the oligonucleotides in the library comprises two random domains flanking the antisense binding domain.

14. The aptamer selection system according to claim 6, wherein the antisense oligonucleotide is biotinlylated.

15. The aptamer selection system according to claim 7, wherein the antisense oligonucleotide is biotinlylated.

16. The aptamer selection system according to claim 8, wherein the antisense oligonucleotide is biotinlylated.

* * * * *